United States Patent
Sams et al.

(10) Patent No.: US 9,849,083 B2
(45) Date of Patent: Dec. 26, 2017

(54) SUBLINGUAL ADMINISTRATION OF STATINS

(71) Applicant: LondonPharma Ltd., Norwich, Norfolk (GB)

(72) Inventors: Martin James Sams, Norwich (GB); Juliet Victoria High, Norwich (GB); Paul Andrew Jamieson, Norwich (GB); Clive Booles, Norwich (GB)

(73) Assignee: LondonPharma Ltd., Norwich, Norfolk (GB)

( * ) Notice: Subject to any disclaimer, the term of this patent is extended or adjusted under 35 U.S.C. 154(b) by 0 days.

(21) Appl. No.: 14/365,798

(22) PCT Filed: Dec. 14, 2012

(86) PCT No.: PCT/GB2012/053135
§ 371 (c)(1),
(2) Date: Jun. 16, 2014

(87) PCT Pub. No.: WO2013/088161
PCT Pub. Date: Jun. 20, 2013

(65) Prior Publication Data
US 2015/0328142 A1 Nov. 19, 2015

(30) Foreign Application Priority Data
Dec. 14, 2011 (GB) .................................. 1121503.5

(51) Int. Cl.
| A61K 31/47 | (2006.01) |
| A61K 9/00 | (2006.01) |
| A61K 31/22 | (2006.01) |
| A61K 31/366 | (2006.01) |
| A61K 31/40 | (2006.01) |
| A61K 31/505 | (2006.01) |
| A61K 9/08 | (2006.01) |
| A61K 31/405 | (2006.01) |
| A61K 47/10 | (2017.01) |
| A61K 47/14 | (2017.01) |

(52) U.S. Cl.
CPC ............... *A61K 9/006* (2013.01); *A61K 9/08* (2013.01); *A61K 31/22* (2013.01); *A61K 31/366* (2013.01); *A61K 31/40* (2013.01); *A61K 31/405* (2013.01); *A61K 31/47* (2013.01); *A61K 31/505* (2013.01); *A61K 47/10* (2013.01); *A61K 47/14* (2013.01)

(58) Field of Classification Search
USPC .............................. 514/7.4, 15.6, 15.7, 16.4
See application file for complete search history.

(56) References Cited

U.S. PATENT DOCUMENTS

| 6,200,591 B1 | 3/2001 | Hussain et al. |
| 6,720,001 B2 | 4/2004 | Chen et al. |
| 8,613,950 B2 | 12/2013 | Serno et al. |
| 2002/0107265 A1 | 8/2002 | Chen et al. |
| 2003/0086948 A1 | 5/2003 | Benameur et al. |
| 2003/0095925 A1* | 5/2003 | Dugger, III .......... A61K 9/0056 424/43 |
| 2003/0100493 A1 | 5/2003 | Weiss |
| 2003/0162827 A1 | 8/2003 | Venkataram et al. |
| 2005/0025714 A1 | 2/2005 | Dugger, III |
| 2006/0035905 A1 | 2/2006 | Jiang et al. |
| 2007/0031349 A1 | 2/2007 | Monteith et al. |
| 2007/0122355 A1 | 5/2007 | Monteith et al. |
| 2008/0249096 A1 | 10/2008 | Serno et al. |
| 2010/0209541 A1 | 8/2010 | Dugger, III |
| 2011/0184057 A1 | 7/2011 | Mundy et al. |
| 2011/0257149 A1* | 10/2011 | Perovitch ............... A61K 47/10 514/210.02 |
| 2011/0263606 A1 | 10/2011 | Zerbe et al. |
| 2012/0027879 A1 | 2/2012 | Dugger, III |
| 2012/0270933 A1* | 10/2012 | Phelps ................. A61K 9/0095 514/460 |
| 2013/0143894 A1 | 6/2013 | Bergstrom et al. |
| 2013/0199519 A1 | 8/2013 | Dugger, III |
| 2014/0200516 A1 | 7/2014 | Dugger, III |

FOREIGN PATENT DOCUMENTS

| DE | 10 2005 009 240 | 9/2006 |
| JP | 2003 192574 | 7/2003 |
| WO | WO 99/66933 | 12/1999 |
| WO | WO 01/28555 | 4/2001 |
| WO | WO 02/05820 | 1/2002 |
| WO | WO 2004/019903 | 3/2004 |
| WO | WO 2005/077374 | 8/2005 |
| WO | WO 2007/002125 | 1/2007 |
| WO | WO 2007/125339 | 11/2007 |

(Continued)

OTHER PUBLICATIONS http://www.cochrane.org/CD004816/VASC__statins-primary-prevention-cardiovascular-disease; Jan. 31, 2013.*
Tiwari et al., "*Statins Therapy: A review on conventional and novel formulation approaches*", Journal of Pharmacy and Pharmacology 2011, Pharmaceutical Press GBR, vol. 63 No. 8, Aug. 2011, pp. 983-998, XP002690987, ISSN: 0022-3573, p. 991, col. 2, paragraph 3.
PCT/GB2012/053135 International Search Report dated Feb. 12, 2013 (3 pages).

(Continued)

*Primary Examiner* — Pancham Bakshi
(74) *Attorney, Agent, or Firm* — Brinks Gilson & Lione; G. Peter Nichols (57) ABSTRACT

The invention provides a pharmaceutical composition for the transmucosal delivery of a statin, said composition comprising a statin and a carrier in which said statin is soluble or forms a suspension or emulsion. The invention also provides a pharmaceutical composition comprising a statin for use in inhibiting cholesterol synthesis in vivo, where in said use said composition is delivered by the transmucosal route.

20 Claims, 2 Drawing Sheets

(56) References Cited

FOREIGN PATENT DOCUMENTS

| WO | WO 2010/098906 | 9/2010 |
|----|----------------|--------|
| WO | WO 2011/156405 | 12/2011 |

OTHER PUBLICATIONS

PCT/GB2012/053135 International Preliminary Report on Patentability dated Jan. 29, 2014 (8 pages).
PCT/GB2012/053184 International Search Report dated May 7, 2013 (4 pages).

* cited by examiner

SUBLINGUAL ADMINISTRATION OF STATINS

This application claims priority to International Application No. PCT/GB2012/053135 filed Dec. 14, 2012 and Great Britain Patent Appln. 1121503.5 filed Dec. 14, 2011, the entire contents of each are incorporated herein by reference.

FIELD OF THE INVENTION

The invention relates to improved methods of delivery for statins.

BACKGROUND

The development of drug delivery routes remains an important element in the progress of the pharmaceutical sciences. Once an active compound has been identified, the design of delivery mechanisms must overcome challenges of transporting the medicament to the required site of action in the body whilst addressing issues including shelf life, bioavailability, toxicity, and patient compliance. All of these challenges must be overcome to achieve the desired therapeutic effect. Amongst the drug delivery options, oral administration is by far the most common route, with other options including injection, inhalation, topical or transmucosal administration.

The oral delivery route faces perhaps the most challenging route for a pharmaceutical to reach the final site of action: the composition is prone to loss from the mouth or stomach (e.g. by spitting or vomiting); the composition must survive the acidic and enzymatically-active environment of the stomach; if not absorbed in the stomach, the medicament must survive the action of bile salts and further intestinal and bacterial enzymatic action within the intestinal tract, be able to cross from the lumen of the gut to the intestinal wall for absorption, and then survive the degradation processes of the liver following transport by the hepatic portal system, often resulting in poor availability due to the first pass effect. In addition, some patients can't take (or don't like taking) tablets, a common form for oral dosing. Despite these challenges, the oral route of drug administration remains the most common.

Statins are HMG-CoA reductase inhibitors. HMG-CoA reductase is the rate-controlling enzyme in the biosynthesis of cholesterol in the liver. Thus statins can be used to lower cholesterol levels in an individual, especially those with hypercholesterolaemia. Increased cholesterol levels have been associated with cardiovascular disease and statins are therefore used in the prevention and management of such diseases. To date, statins have been administered exclusively orally, and a number of side-effect issues have arisen. Firstly, oral delivery provides quite variable levels of absorption for a particular statin dose, both intra-subject (possibly dependent on e.g. gastric content) and inter-subject. Secondly, a number of adverse effects have been reported, such as gastrointestinal adverse effects, raised liver enzymes and muscle problems—such as myalgias, myopathy and myositis. In the extreme, rhabdomyolysis with acute renal failure may occur.

It is among the objectives of the present invention to attempt a solution to these problems.

SUMMARY OF THE INVENTION

The inventors have surprisingly identified formulation conditions via which pharmaceutical compositions comprising a statin—whether lipophilic or hydrophilic—can be successfully delivered to subjects by the sublingual transmucosal route, thereby avoiding at least the unwanted gastrointestinal adverse effects that arise with oral delivery (and possibly also the adverse muscle effects). In addition, sublingual transmucosal delivery appears to provide more consistent absorption (intra- and inter-subject) than oral delivery. Furthermore, such sublingual transmucosal delivery is beneficial over the oral route in which the statin may be lost from the mouth or stomach (e.g. spitting or vomiting) or in which taking tablets is difficult or not possible. The inventors have thus enabled the use of a statin for inhibiting cholesterol synthesis in vivo, wherein said use said composition is delivered by the sublingual transmucosal route. By utilising delivery by spray the inventors have identified further improvements to delivery which are mentioned herein.

Accordingly, the invention provides a pharmaceutical composition for the transmucosal delivery of a statin, said composition comprising a statin and a carrier in which said statin is soluble or forms a suspension or emulsion. In particular the invention provides a pharmaceutical composition for use in a method of preventing or treating hypercholesterolaemia, dyslipidaemia, cardiovascular disease or cancer; or an effect of any of these conditions, in an individual, wherein the composition is delivered by sublingual administration as a spray, and wherein said composition comprises:
  a statin; and
  a carrier in which said statin is soluble or forms a suspension or emulsion.

In an aspect of the invention said statin is lipophilic, preferably simvastatin, atorvastatin, lovastatin, pitavastatin, or a salt thereof, said carrier comprises an oil that comprises a glyceride, and said statin is solubilised in said carrier.

In an alternative aspect of the invention said statin is hydrophilic, preferably fluvastatin, pravastatin, rosuvastatin, or a salt thereof, said carrier comprises an aqueous solution, and said statin is solubilised in said carrier (provided that if the statin is pravastatin then the composition has a pH of at least 8 and is substantially free of ethanol).

In optional embodiments of these aspects, the composition further comprises a co-solvent, preferably wherein said co-solvent comprises an alcohol, preferably ethanol, 2-(2-ethoxyethoxy)-ethanol, or propylene glycol.

In a further aspect of the invention said statin is lipophilic, preferably simvastatin, atorvastatin, lovastatin, pitavastatin, or a salt thereof, said carrier comprises an aqueous solution, and said statin is suspended or emulsified in said carrier.

In yet a further aspect of the invention, said statin is hydrophilic, preferably fluvastatin, pravastatin, rosuvastatin, or a salt thereof, said carrier comprises an oil that comprises a glyceride, and said statin is suspended or emulsified in said carrier (provided that if the statin is pravastatin then the composition is substantially free of ethanol).

Where the carrier comprises an oil that comprises a glyceride, said oil preferably comprises a triglyceride and/or a macrogolglyceride. In the former instance, said oil preferably comprises a medium chain triglyceride (Ph Eur), preferably a miglyol, preferably miglyol 810, miglyol 812, miglyol 818, miglyol 829 or miglyol 840. In the latter instance, said oil preferably comprises caprylocaproyl macrogolglycerides (Ph Eur).

In preferred embodiments of any aspect of the invention, the composition further comprises a preservative, preferably ethanol, potassium sorbate, benzalkonium chloride, or methyl, ethyl or propyl parahydroxybenzoate or a sodium salt thereof, and/or an antioxidant.

In preferred embodiments of any aspect of the invention, the composition further comprises a flavouring agent and/or a sweetener. Where the carrier of the composition comprises an oil that comprises a glyceride, the composition preferably comprises a lipophilic flavouring agent, preferably menthol, vanillin or an essential oil (preferably orange oil, lemon oil, clove oil, peppermint oil, spearmint oil or aniseed oil).

Alternatively, where the carrier of the composition comprises an aqueous solution, preferably said flavouring agent comprises (i) a water-soluble flavouring agent and/or (ii) a lipophilic flavouring agent that is solubilised by means of a water-miscible oil-based solvent, and/or preferably said sweetener is water-soluble. Preferably said lipophilic flavouring agent comprises menthol, peppermint oil, lemon oil or aniseed oil and/or said water-miscible oil-based solvent comprises macrogolglycerol ricinoleate (Ph Eur). Preferably, said sweetener comprises sucralose, sorbitol, glycerol or sodium saccharin.

Also provided is a composition according to the invention that is comprised within a container that comprises a delivery device, preferably wherein said delivery device dispenses the composition as a spray.

Further provided is a pharmaceutical composition comprising a statin for use in inhibiting cholesterol synthesis in vivo, where in said use said composition is delivered by the transmucosal route, and a composition according to the invention for use in inhibiting cholesterol synthesis in vivo, where in said use said composition is delivered by the transmucosal route.

DETAILED DESCRIPTION OF THE INVENTION

All references to transmucosal delivery/administration herein, are preferably by sublingual delivery by spray.

The invention relates to a pharmaceutical composition for the transmucosal delivery of a statin. A statin is any inhibitor (e.g. competitive) of HMG-CoA (3-hydroxy-3-methyl-glutaryl-CoA reductase) reductase. Particular statins that are envisaged are the well-known statins simvastatin, atorvastatin, lovastatin and pitavastatin (which are lipophilic statins) and fluvastatin, pravastatin and rosuvastatin (which are hydrophilic statins). All of these medicaments have well-defined chemical structures that are widely published in drug reference sources (e.g. Martindale).

The composition comprises a carrier in which the statin is soluble or forms a suspension or emulsion, preferably wherein more than 50% of the statin is solubilised or suspended/emulsified (respectively) in said carrier, preferably wherein at least 75% of the statin is solubilised or suspended/emulsified, more preferably at least 85%, more preferably at least 90%, most preferably at least 99% (and preferably at a temperature between 5° C. and 40° C.).

Preferably, the carrier is liquid at between 5° C. and 40° C., and particularly is it preferred that the carrier is liquid at between 15° C. and 40° C.

Preferably, the statin is present in the carrier at a concentration providing a required dose in a volume of no more than 1000 microliters of composition, more preferably in a volume of no more than 500 microliters, more preferably in a volume of no more than 200 microliters of composition, and most preferably in a volume of no more than 100 microliters of composition. In preferred embodiments the statin is present in said composition at a concentration of at least 5 mg/ml, preferably at least 10 mg/ml, more preferably at least 25 mg/ml, more preferably at least 50 mg/ml (and optionally at least 80 m/ml, at least 100 mg/ml, or at least 150 mg/ml).

A further preferred feature is that the statin is stable in the composition, both with respect to physicochemical aspects such as remaining in solution or suspension/emulsion (as required) and in terms of chemical (including biochemical) degradation of the statin over time. It is particularly preferred, therefore, that the statin is stable within the composition, to pharmaceutically-acceptable limits, over a period of at least one month, preferably at least 2 months, more preferably at least 3 months, more preferably at least 6 months, more preferably at least 12 months, more preferably at least 18 months, more preferably at least 2 years, more preferably at least 3 years, more preferably at least 4 years, and most preferably at least 5 years, whilst kept at a temperature(s) between 4° C. and 40° C. and under the Relative Humidity conditions defined in the relevant ICH guidelines (preferably up to 25° C. or 30° C.).

In one embodiment the period of time from preparation of the composition to its administration is at least one month, at least 2 months, at least 6 months, at least 12 months, at least 18 months, at least 2 years or at least 3 years.

Compositions Solubilising Lipophilic Statins

In an aspect of the invention the statin is lipophilic, preferably simvastatin, atorvastatin, lovastatin, pitavastatin, or a salt thereof, and the statin is solubilised in a carrier that comprises (or consists essentially of) an oil that comprises (or consists essentially of) a glyceride. Preferably, the statin is simvastatin. This statin is typically dosed orally at 10-80 mg and it is hydrolysed in vivo to its active beta-hydroxy-acid form. Therefore, in this aspect of the composition of the invention, simvastatin is preferably provided at a concentration of at least 5 mg/ml, more preferably at least 50 mg/ml (enabling e.g. a dose of 5 mg to be delivered with a 100 μl actuation). In particularly preferred embodiments the composition comprises a carrier that comprises: a macrogolglyceride (e.g. comprising caprylocaproyl macrogolglycerides Ph Eur); or a triglyceride (especially a medium chain triglyceride) in combination with a co-solvent (especially an alcohol, most preferably ethanol or 2-(2-ethoxyethoxy)-ethanol).

Surprisingly, the use of a carrier that comprises a macrogolglyceride enables lipophilic statins (e.g. simvastatin) to be solubilised at high concentration without the use of a co-solvent. Furthermore, it has surprisingly been found that transmucosal delivery of simvastatin, using the composition of the invention, provided higher conversion to the active form—simvastatin acid—than the corresponding conversion rates following oral administration. It is thought that the inactive, precursor simvastatin molecule has greater potency with respect to adverse muscle effects than simvastatin acid, so this effect means that transmucosal delivery of simvastatin appears to be safer (in relation to muscle problems) than oral delivery. In one embodiment the individual is susceptible to the adverse muscle effects of statins, and preferably the individual is susceptible to adverse muscle effects when given an oral administration of a statin.

Compositions Solubilising Hydrophilic Statins

In an alternative aspect of the invention the statin is hydrophilic, preferably fluvastatin, pravastatin, rosuvastatin, or a salt thereof, and the statin is solubilised in a carrier that comprises (or consists essentially of) an aqueous solution (including water itself), provided that if the statin is pravastatin then the composition has a pH of at least 8 and is substantially free of ethanol.

In preferred embodiments the statin is pravastatin (preferably pravastatin sodium). This statin is typically dosed orally at 10-40 mg. Therefore, in this aspect of the composition of the invention, pravastatin is preferably provided at a concentration of at least 5 mg/ml, more preferably at least 50 mg/ml (enabling e.g. a dose of 5 mg to be delivered with a 100 µl actuation), more preferably at least 100 mg/ml (enabling e.g. a dose of 10 mg to be delivered with a 100 µl actuation). It is particularly preferred that such a composition comprising pravastatin further comprises a flavouring agent and/or a sweetener (see below).

In alternative embodiments the statin is fluvastatin (preferably fluvastatin sodium). This statin is typically dosed orally at 20-80 mg. Therefore, in this aspect of the composition of the invention, fluvastatin is preferably provided at a concentration of at least 5 mg/ml, more preferably at least 25 mg/ml (enabling e.g. a dose of 2.5 mg to be delivered with a 100 µl actuation), more preferably at least 50 mg/ml. In particularly preferred embodiments the composition comprises a co-solvent (especially an alcohol, most preferably ethanol or propylene glycol) and/or the composition has a pH of at least 8, preferably a pH of 8-10. It is particularly preferred that such composition comprising fluvastatin further comprises a flavouring agent and/or a sweetener (see below).

It is surprising to find that such essentially aqueous compositions have been used to successfully deliver statins by the transmucosal route given the expected propensity for such hydrophilic compositions to be washed down into the gastrointestinal tract.

Co-Solvents

In embodiments of the above compositions of the invention said composition further comprises a co-solvent i.e. any agent that increases the solubility of the statin in the carrier. In preferred embodiments said co-solvent comprises (or consists essentially of) an alcohol, preferably ethanol, 2-(2-ethoxyethoxy)-ethanol, or propylene glycol. A co-solvent can be used at between 1% and 49% w/w or v/v, more preferably between 1% and 40%, most preferably between 5% and 35%. Clearly, where the statin is pravastatin then the co-solvent does not comprise ethanol.

Suspensions/Emulsions

In other aspects of the invention the composition of the invention comprises a statin and a carrier in which said statin forms a suspension or emulsion.

In particular embodiments the statin is lipophilic, preferably simvastatin, atorvastatin, lovastatin, pitavastatin, or a salt thereof, and the statin is suspended or emulsified in a carrier that comprises (or consists essentially of) an aqueous solution (including water itself).

In alternative embodiments the statin is hydrophilic, preferably fluvastatin, pravastatin, rosuvastatin, or a salt thereof, and the statin is suspended or emulsified in a carrier that comprises (or consists essentially of) an oil that comprises (or consists essentially of) a glyceride, provided that if the statin is pravastatin then the composition is substantially free of ethanol.

Carriers Comprising an Oil that Comprises a Glyceride

Such carriers might comprise (or consists essentially of) an oil comprising a monoglyceride, a diglyceride and/or (and preferably) a triglyceride. Preferred oils include Glycerol mono-oleates (Ph Eur); Fractionated Palm Kernel Oil (Ph Eur); Hydrogenated Cottonseed Oil (Ph Eur); Omega-3-Marine Triglycerides (Ph Eur); Fish Oil, Rich in Omega-3-Acids (Ph Eur); Cod Liver Oil (Ph Eur).

Preferred oils that comprise (or consist essentially of) a triglyceride include Refined Maize Oil (Ph Eur), Virgin Castor Oil (Ph Eur), Refined Olive Oil (Ph Eur), Refined Rapeseed Oil (Ph Eur), Vegetable Fatty Oils (Ph Eur) and, in particular, Medium Chain Triglycerides (Ph Eur).

Medium chain length triglycerides are defined in the European Pharmacopoeia Monograph 0868, as:

A mixture of triglycerides of saturated fatty acids, mainly of caprylic acid (octanoic acid, $C_8H_{16}O_2$) and of capric acid (decanoic acid, $C_{10}H_{20}O_2$). Medium-chain triglycerides are obtained from the oil extracted from the hard, dried fraction of the endosperm of Cocos nucifera L. or from the dried endosperm of Elaeis guineensis Jacq. When Medium-chain Triglycerides are prepared from the endosperm of Cocos nucifera L., the title Fractionated Coconut Oil may be used. Medium chain length triglycerides have a minimum 95.0 percent of saturated fatty acids with 8 and 10 carbon atoms. Further chemical and physical properties are described in the European Pharmacopoeia Monograph 0868, and equivalent documents.

In preferred embodiments the oil comprises a miglyol, preferably miglyol 810, miglyol 812, miglyol 818, miglyol 829 or miglyol 840

In preferred embodiments the carrier comprises an oil comprising a macrogolglyceride, such as Linoleoyl Macrogolglycerides (Ph Eur), Oleoyl Macrogolglycerides (Ph Eur) or, preferably, caprylocaproyl macrogolglycerides (Ph Eur).

Caprylocaproyl macrogolglycerides are defined in the European Pharmacopoeia Monograph 1184, as:

Caprylocaproyl macrogolglycerides are mixtures of monoesters, diesters and triesters of glycerol and monoesters and diesters of macrogols with a mean relative molecular mass between 200 and 400. They are obtained by partial alcoholysis of medium-chain triglycerides using macrogol or by esterification of glycerol and macrogol with caprylic acid and capric acid or a mixture of glycerol esters and condensates of ethylene oxide with caprylic acid (octanoic acid) and capric acid (decanoic acid). They may contain free macrogols.

Further Optional Components

In preferred embodiments of any of said compositions, the composition further comprises a preservative (i.e. any agent that kills or inhibits the growth of a microorganism), preferably ethanol, potassium sorbate, benzalkonium chloride, or methyl, ethyl or propyl parahydroxybenzoate or a sodium salt thereof, and/or an antioxidant (e.g. butylated hydoxyanisole (BHA) or butylated hydoxytoluene (BHT) for compositions wherein the carrier comprises an oil comprising a glyceride). Clearly, where the statin is pravastatin then the preservative does not comprise ethanol. Preferably, said preservative and/or said antioxidant is present at an effective concentration, preferably at a concentration of at least 0.1% w/w or v/v, preferably at least 0.5%, and preferably at a concentration within published safety limits.

In preferred embodiments of any of said compositions, the composition further comprises a flavouring and/or a sweetener.

In an aspect of the invention, wherein the carrier of the composition comprises an oil that comprises a glyceride, the composition comprises a lipophilic flavouring agent, such as menthol, vanillin or an essential oil (e.g. orange oil, lemon oil, clove oil, peppermint oil, spearmint oil, or aniseed oil), preferably at a concentration of at least 0.1% v/v, preferably at least 0.5%.

Fluvastatin and pravastatin have a bitter and unpleasant taste. Therefore, in another aspect of the invention, wherein the carrier of the composition comprises an aqueous solution, the composition comprises a flavouring agent comprising (or consisting essentially of) a water-soluble flavouring agent and/or a lipophilic flavouring agent that is solubilised by means of a water-miscible oil-based solvent. Such a composition might alternatively or additionally comprise a water-soluble sweetener. In preferred embodiments the lipophilic flavouring agent comprises (or consists essentially of) menthol, peppermint oil, lemon oil or aniseed oil—it has surprisingly been found that these particular flavourings can be solubilised in an aqueous solution when using a water-miscible oil-based solvent. The flavouring agent is preferably present at a concentration of at least 0.1% w/w, preferably at least 0.5% and optionally up to 2%. The water-miscible oil-based solvent is preferably present at a concentration of at least 1% w/w, preferably at least 5% and optionally up to 10% or up to 25%. A particularly effective water-miscible oil-based solvent comprises (or consists essentially of) macrogolglycerol ricinoleate (Ph Eur). Preferably such a solvent is not used above 17% w/w. Macrogolglycerol Ricinoleate is defined in the European Pharmacopoeia Monograph 1082, as:

Contains mainly ricinoleyl glycerol ethoxylated with 30 to 50 molecules of ethylene oxide (nominal value), with small amounts of macrogol ricinoleate and of the corresponding free glycols. It results from the reaction of castor oil with ethylene oxide.

The water-soluble sweetener preferably comprises (or consists essentially of) sucralose, sorbitol, glycerol or sodium saccharin, and is preferably present at a concentration of at least 0.05% w/w, preferably at least 0.1%.

Particularly good taste improvement and/or masking of the bitterness of these statins was achieved using a combination of a flavouring agent (preferably a fruit or mint flavour and/or lipophilic [solubilised by means of a water-miscible oil-based solvent]) and a sweetener (preferably water-soluble, preferably sucralose).

Potentially Excluded Components

Pravastatin (sodium salt) was found to react with ethanol so ethanol is excluded from compositions comprising pravastatin. There might be other reasons to optionally exclude ethanol (and hence in some preferred embodiments the composition is substantially free of ethanol e.g. comprises <1% w/w or v/v ethanol, more preferably less than 0.5% ethanol, and most preferably less than 0.1% ethanol), for example where the composition is to be used in cultural or religious contexts where ethanol intake is not permitted. In one embodiment the composition has 0 to 30% ethanol, such as less than 25%, less than 20%, less than 10% or less than 5% ethanol.

Furthermore, it is possible to exclude propellants as these can be irritating to the mucosa. In optional embodiments, therefore, the composition of the invention is substantially free of propellant e.g. comprises <1% w/w or v/v propellant, more preferably less than 0.5% propellant, and most preferably less than 0.1% propellant.

In one embodiment the composition does not comprise N-methylpyrrolidone or comprises less than 10%, less than 1% or less than 0.1% N-methylpyrrolidone.

Delivery Devices

Preferably the compositions of the present invention are comprised within a container that comprises a delivery device; the device can dispense the composition as a single or multiple discharge. Preferably the device is non-pressurised.

The compositions of the present invention can be delivered as a liquid bolus or, preferably, as a spray. Preferably, said spray comprises liquid droplets having a mean diameter of at least about 10 microns, preferably at least 20 microns, more preferably from about 20 to about 200 microns, most preferably from about 20 to about 100 microns. Preferably the compositions are delivered as liquid droplets that have a size distribution of from about 5 microns to about 500 microns, preferably from about 10 microns to about 200 microns, more preferably from about 20 microns to about 100 microns. Choice of these (larger) droplet sizes means that the droplets have larger weight and this is preferable in the invention because a larger weight increases the chances that the droplet, and therefore the statin, falls rapidly onto the mucosa thereby reducing the possibility that the droplets become entrained in breath and expelled from the mouth, or taken into the lungs.

It is particularly preferred that each individual or successive dose has a volume of less than 1000 microliters. The use of small dose volumes reduces the likelihood that the composition will be swallowed, or spat out, by the patient. The likelihood is reduced further by use of smaller volumes (especially in the paediatric context) and so in further preferred embodiments, each dose has a volume of less than 600 microliters; less than 500 microliters; less than 400 microliters; less than 300 microliters; less than 200 microliters; or even less than 100 microliters. Smaller volumes are especially preferred for paediatric use.

Preferably, the delivery device according to these aspects comprises a spray device, preferably a non-pressurised spray device, and especially a pump spray device. The use of a pump spray device increases the area of mucosa to which the composition is applied, thereby increasing absorption and minimising the likelihood that the medicament is swallowed.

In one embodiment the composition has (consists of) either 1 or 2 liquid phases.

Outcomes

The invention also provides a pharmaceutical composition comprising a statin (such as any of the compositions of the present invention) for use in inhibiting cholesterol synthesis in vivo, where in said use said composition is delivered by the transmucosal route (such as via the nasal, buccal or sublingual route, preferably by the sublingual route). By inhibiting cholesterol synthesis, statins act for example to reduce total cholesterol blood levels, primarily by lowering low-density lipoprotein (LDL) and very-low-density lipoprotein (VLDL) blood levels. They can also increase high-density lipoprotein (HDL) blood levels. The invention thus provides said composition for any of these specific effects, as well as for the treatment of hyperlipidaemias such as hypercholesterolaemia (i.e. reduction in circulatory cholesterol levels in an individual with a clinically abnormally high level of blood cholesterol) and/or the prevention, management or treatment of a cardiovascular disease (including atherosclerosis).

The invention thereby also provides a method of treating a human or animal (preferably mammal) subject in need of a statin comprising the administration to said subject of a therapeutically effective amount of a composition comprising a statin, whereby administration is by the transmucosal route (such as via the nasal, buccal or sublingual route, preferably by the sublingual route). In such a method the subject may, for example, have a hyperlipidaemia (e.g. hypercholesterolaemia) or be suffering from (or is at risk of) a cardiovascular disease.

Advantageous Pharmacokinetics

The advantageous pharmacokinetics discovered by the inventors means that administration according to the invention is particularly suited to certain patient groups. Thus in preferred embodiments the invention relates to treating patients for whom it is important to avoid variability in dosage and/or who are susceptible to certain conditions or side effects.

The invention concerns in particular prevention or treatment of adults (at least 16 years old), adolescents (from 10 to 15 years old) and children (aged 10 or less) with hypercholesterolaemia or mixed dyslipidaemia, preferably when response to dietary change or exercise or weight reduction is inadequate. The invention relates to prevention or treatment of homozygous familial hypercholesterolaemia. The invention relates to reduction of cardiovascular mortality and morbidity in patients with atherosclerotic cardiac disease or diabetes mellitus, where the patients may optionally have normal or increased cholesterol levels. The invention relates to improved survival in patients with cancer, as well as primary and/or secondary prevention of cancer.

Preferred individuals to be treated include those that cannot, or are unwilling to, swallow tablets. The individual may have a gastrointestinal condition, for example dysphagia (difficulty in swallowing) or may suffer from nausea and/or heartburn when given tablets. The patient may have a gastrointestinal obstruction, such as in the upper part of the gastrointestinal tract. The patient may be a child, and thus be less able to take a tablet. The patient may have a preference for a sublingual spray or may have reduced consciousness or be unconscious.

In one embodiment the individual does not undergo heart surgery within 1, 5, 20 or 30 days of the administration. In another embodiment the individual is not in hospital and/or is not under the care of a medical practitioner. In one embodiment the individual is on long term statin therapy, for example has had at least one administration every 15 or 30 days for more than 200, 300 or 500 days.

One reason that oral administration can lead to variability in dosage is due to differences in activity of the CYP3A4 intestinal protein on statins. In one embodiment the individual is given 2, 3, 4, 5 or 6 to 10 administrations according to the invention, and all of these administrations have an effective dosage which differs from the first administration by less than 15% of the effective dosage of the first administration.

In a preferred embodiment the $T_{max}$ (time to maximal plasma concentration) is less than 2 hours from administration, preferably less than 1 hour or less than 0.5 hours.

EXAMPLES

Example 1

Simvastatin Formulation Summary

Formulation for simvastatin was attempted firstly with water and secondly in Miglyol 810 (medium-chain triglycerides Ph Eur). The formulation in water did not dissolve and formed a milky white precipitate (suspension). The second formulation in Miglyol dissolved up to about 5 mg/ml. The use of ethanol (20% v/v) as a co-solvent allowed an increased concentration of simvastatin to be solubilised, up to about 80 mg/ml. Ethanol also acts as a preservative. Butylated HydroxyToluene (BHT) or Butylated HydroxyAnisole (BHA) was used as an anti-oxidant and menthol was used for flavouring.

A GMP batch (11-086) was made with simvastatin provided at 50 mg/ml:

| Simvastatin 5 mg per 0.1 ml actuation (Batch size 2000 ml) | |
|---|---|
| Material | Weight (g) |
| Simvastatin USP | 100.0 |
| Ethanol, Anhydrous Ph Eur | 400.0 |
| Butylated Hydroxyanisole Ph Eur | 10.0 |
| Levomenthol Ph Eur | 14.0 |
| Medium Chain Triglycerides Ph Eur | To vol |

Solubility and stability were acceptable after at least 2 months (5° C. and 25° C.). This batch was tested in the clinic (see later section).

It was found that simvastatin could also be solubilised up to about 80 mg/ml by using 15% v/v Transcutol HP (diethylene glycol monoethyl ether Ph Eur) instead of 20% v/v ethanol or by using Labrasol (caprylocaproyl macrogolglycerides Ph Eur) instead of Miglyol. Note that diethylene glycol monoethyl ether is defined in the European Pharmacopoeia Monograph 1198 as: 2-(2-Ethoxyethoxy) ethanol, produced by condensation of ethylene oxide and alcohol, followed by distillation. [In the absence of ethanol an alternative preservative could be used e.g. propyl parabens.]

Example 2

Pravastatin Formulation Summary

Pravastatin (sodium salt) was found to react with ethanol so ethanol was excluded from all pravastatin formulations. Formulation of pravastatin sodium in Miglyol 810 formed a suspension but this statin did dissolve in aqueous-based formulations, up to at least 150 mg/ml. Pravastatin undergoes hydrolysis at a pH less than 8 so formulations should have a pH of 8 or more throughout product life.

A GMP batch (11-087) was made with pravastatin provided at 50 mg/ml:

| Pravastatin 5 mg per 0.1 ml actuation (Batch size 2000 ml) | |
|---|---|
| Material | Weight (g) |
| Pravastatin sodium Ph Eur | 100.0 |
| Sodium methyl hydroxybenzoate Ph Eur | 8.0 |
| Disodium Edetate Ph Eur | 2.0 |
| Saccharin Sodium Ph Eur | 2.0 |
| Purified water | To vol |

Solubility and stability were acceptable after at least 2 months (5° C. and 25° C.). This batch was tested in the clinic (see later section).

The taste acceptance results from the clinic were as follows (figures represent number of subjects):

| 50 mg/dose | | | | |
|---|---|---|---|---|
| | No taste | Present but not unpleasant | Moderately unpleasant | Very unpleasant |
| 5 mins | 0 | 3 | 5 | 0 |
| 0.5 h | 5 | 3 | 0 | 0 |
| 1.0 h | 8 | 0 | 0 | 0 |

| 100 mg/dose | | | | |
|---|---|---|---|---|
| | No taste | Present but not unpleasant | Moderately unpleasant | Very unpleasant |
| 5 mins | 0 | 1 | 5 | 2 |
| 0.5 h | 5 | 3 | 0 | 0 |
| 1.0 h | 8 | 0 | 0 | 0 |

Further formulation work was carried out to improve the taste results from the clinic. Sodium saccharin as a sweetener gave some improvement in taste but alternative components were tested, bearing in mind that the product would be taken by a patient daily so such components should not only be pharmacopeial but also e.g. low calorific value and non-cariogenic.

In terms of sweeteners, sorbitol, glycerol and maltitol were miscible and improved palatability, though maltitol had limited stability. Sucralose showed notably good results, and is advantageous because it is only required in very small quantities (e.g. 0.05-0.1%) and is non-cariogenic. Aspartame, Acesulfame K and saccharin itself are insoluble in water. Water-soluble flavours in powdered or liquid form (e.g. strawberry 501094 and orange juice 506304, respectively) gave an improvement in taste (at 0.1-1.0%).

Particularly good improvements in taste were obtained using lipophilic flavours, once conditions had been identified in which select examples could be dissolved within the aqueous carrier. Cremophor EL (macrogolglycerol ricinoleate Ph Eur) was identified as a component that was able to maintain menthol, peppermint oil, aniseed and lemon oil in solution. These flavours were firstly mixed at 1% w/w with Cremophor EL, and the resultant combination then with water (10% w/w in purified water). Conversely, vanillin, orange oil and clove oil (after combination with Cremophor EL) did not remain miscible when mixed with water. Note that vanillin also degraded in Cremophor EL, rendering it unusable. Note that Cremophor EL did not mix well with water above ~17% and should therefore not be used above this concentration. The action of Cremophor EL here is that of a water-miscible oil-based solvent.

Particularly good taste improvement and/or masking of the bitterness of pravastatin was achieved if a combination of a flavouring agent and a sweetener (preferably water-soluble) was used. An ideal combination is one using a fruit flavour (e.g. lemon oil, solubilised using Cremophor EL) with sucralose.

Example 3

Fluvastatin Formulation Summary

Fluvastatin (sodium salt) was found to form a suspension in Miglyol 810 but this statin did dissolve in aqueous-based formulations, up to at least 25 mg/ml using ethanol or propylene glycol (both at 20% w/w) as a co-solvent.

A GMP batch (11-126) was made with fluvastatin provided at 25 mg/ml:

| Fluvastatin 2.5 mg, per 0.1 ml actuation (Batch size 2000 ml) | | |
|---|---|---|
| Material | Weight (g) | % w/w |
| Fluvastatin Sodium USP | 50.0 | 2.5 |
| Ethanol anhydrous Ph Eur | 400.0 | 20.0 |
| Purified water Ph Eur | To vol | 77.5 |

Solubility and stability were acceptable after at least 1 month (5° C. and 25° C.). This batch was tested in the clinic (see later section).

Note that taste analysis from the clinic found fluvastatin to be very bitter, so an improvement in the flavour is preferable; the techniques used for pravastatin may be employed—fluvastatin was found to remain in solution when mixed with 10% Cremophor. The most promising taste results were obtained using lemon oil, menthol or peppermint oil (all via Cremophor EL) in combination with 0.05% sucralose. Preliminary analysis shows that solubility and/or stability can be optimised at a pH of 8-10.

Example 4

Pharmacokinetic Studies

A confidential phase 1, single centre, open label, randomised crossover trial was carried out to evaluate the rate and extent of absorption of various sublingual formulations of statins in healthy male subjects.

Objectives

The primary objectives of this study were to:
assess the sublingual absorption of the study medications
establish dose proportionality between different doses administered The secondary objectives of this study were to:
establish the safety, tolerability, local tolerance and taste acceptance of the study medications Methodology/Study Design Subjects were required to provide their written informed consent prior to any study related procedures being conducted. Subjects were screened for eligibility within 28 days of first study admission on Day-1. Eligible subjects were required to participate in two study treatment periods, each at a different dose level of the same statin with a washout period of at least 24 hours between the study periods. For each treatment period, subjects were admitted to the clinical research unit (CRU) the evening prior to dosing. Subjects received their treatments in a randomised way. Subjects were closely monitored in the clinic for at least 8 hours after dosing. After the last treatment period, subjects returned for a post study follow up visit.

Number of Subjects

A total of 24 healthy male subjects were enrolled in the study; 8 subjects for each test product.

Number of Subjects Analysed

All 24 subjects entered and completed the study and were included in the safety and pharmacokinetic populations.

Diagnosis and Main Criteria for Inclusion

Healthy male subjects aged 18-55 of any ethnic origin, with a body mass index (BMI) within the range 18-25, and a minimum weight of at least 55 kg were eligible for the trial. Subjects had to be in good health as determined by a medical history, medical examination, electrocardiogram, laboratory tests, and serology. Subjects had to be willing to complete all required assessments. Prior to any study procedures, subjects were required to understand as well as sign the informed consent form (ICF).

Test Product, Dose and Mode of Administration Batch Number(s)

Simvastatin sublingual spray 5 mg per 100 µl actuation (dosed at 20 mg or 40 mg), batch number 11-086.

Fluvastatin sublingual spray 2.5 mg per 100 µl actuation (dosed at 10 mg or 25 mg), batch number 11-126.

Pravastatin sublingual spray 5 mg per 100 µl actuation (dosed at 20 mg or 40 mg), batch number 11-087.

Duration of Treatment

The duration of the study was approximately 6 weeks for each subject including the screening and follow-up period. Subjects had 2 inpatient treatment periods with a washout period of at least 24 hours between treatments.

Criteria for Evaluation

Pharmacokinetic Variables—

Blood samples were collected for pharmacokinetic (PK) analysis at the following time points: predose (within 60 mins), and 0.5, 1, 1.5, 2, 3, 4, 6 and 8 hours after dosing.

The following pharmacokinetic parameters for all statins were calculated by standard non-compartmental methods for the traditional two stage analysis using WinNonlin Ver 5.0.1: $AUC_{0-t}$, $AUC_{0-\infty}$, $C_{max}$, $T_{max}$, $\lambda_z$, $t_{1/2}$, CL/F, and V/F. SPSS Ver 17.0 was used for the statistical analysis.

Safety Variables—

Safety was evaluated by adverse event (AE) monitoring, evaluation of any medically significant changes, based on physical examination findings, vital signs, and electrocardiograms (ECGs) assessments, clinical laboratory testing, local tolerance and taste acceptance.

Statistical Methods

All statistical analyses were appropriate to the nature and distribution of the data collected. These are detailed in the pharmacokinetic analysis plan (PAP).

Pharmacokinetics

For fluvastatin and pravastatin, pharmacokinetic samples from all treatment periods were analysed for concentrations of the parent compound only. For simvastatin, the active metabolite simvastatin acid was analysed in addition to the parent molecule following initial review of the PK data for the parent. Statistical analysis was based on data from all treatment periods for all subjects that had measurable plasma concentrations studied. Individual subject profiles and mean profiles of the plasma concentration for each active by treatment were produced.

The PK parameters $AUC_{0-t}$, $AUC_{0-\infty}$, $C_{max}$, $T_{max}$, $\lambda_z$, $t_{1/2}$, CL/F, and V/F were listed by treatment for each subject, and where appropriate suitable statistical comparisons were made. Descriptive summaries including n, arithmetic mean, SD, CV (%), geometric mean, 95% CI for the arithmetic mean, median, minimum and maximum were presented for each dose level. $T_{max}$ was summarised using n, median, minimum and maximum values.

Safety Analyses

Safety data was summarised by descriptive methods; continuous variables by summary statistics and categorical data by absolute and relative frequencies.

Summary of Pharmacokinetic Results and Conclusions

Summary PK Parameters for simvastatin sublingual spray and simvastatin acid following simvastatin sublingual spray by dose level -

| Pharmacokinetic Parameter | Summary Statistic | Simvastatin Dose Level 1 (20 mg) | Simvastatin Dose Level 2 (40 mg) | Simvastatin Acid Dose Level 1 (20 mg) | Simvastatin Acid Dose Level 2 (40 mg) |
| --- | --- | --- | --- | --- | --- |
| $AUC_{0-8}$ (ng·h/mL) | Mean | 30.35 | 55.10 | 21.31 | 32.51 |
|  | CV % | 52 | 43 | 31 | 35 |
| $AUC_{0-\infty}$ (ng·h/mL) | Mean | 32.86 | 61.07 | 37.67 | 47.58 |
|  | CV % | 50 | 42 | 39 | 32 |
| $C_{max}$ (ng/mL) | Mean | 8.83 | 17.32 | 6.10 | 9.88 |
|  | CV % | 64 | 47 | 63 | 85 |
| $t_{1/2}$ (h) | Mean | 1.8 | 1.9 | 5.73 | 3.65 |
|  | CV % | 16 | 23 | 87 | 27 |
| $T_{max}$ (h) | Median | 1.88 | 1.88 | 2.19 | 3.88 |
|  | Range | 1.00-3.00 | 1.00-4.00 | 0.50-4.00 | 2.00-8.00 |
| Vz/F (L) | Mean | 1976.16 | 2067.89 | 3961.70 | 4755.81 |
|  | CV % | 51 | 42 | 55 | 36 |
| CL/F (L/h) | Mean | 744.33 | 764.67 | 609.03 | 921.93 |
|  | CV % | 47 | 40 | 39 | 33 |

Summary PK Parameters for fluvastatin and pravastatin by dose level -

| Pharmacokinetic Parameter | Summary Statistic | Fluvastatin Dose Level 1 (10 mg) | Fluvastatin Dose Level 2 (25 mg) | Pravastatin Dose Level 1 (20 mg) | Pravastatin Dose Level 2 (40 mg) |
| --- | --- | --- | --- | --- | --- |
| $AUC_{0-8}$ (ng·h/mL) | Mean | 36.30 | 89.90 | 29.99 | 78.78 |
|  | CV % | 48 | 58 | 31 | 54 |
| $AUC_{0-\infty}$ (ng·h/mL) | Mean | 37.23 | 91.67 | 31.16 | 80.58 |
|  | CV % | 48 | 58 | 29 | 54 |
| $C_{max}$ (ng/mL) | Mean | 34.18 | 88.01 | 12.32 | 44.51 |
|  | CV % | 56 | 77 | 37 | 60 |
| $t_{1/2}$ (h) | Mean | 1.18 | 1.40 | 1.58 | 1.32 |
|  | CV % | 47 | 35 | 41 | 20 |
| $T_{max}$ (h) | Median | 0.56 | 0.57 | 1.33 | 1.29 |
|  | Range | 0.50-1.00 | 0.50-1.00 | 1.00-2.00 | 1.00-2.00 |
| V/F (L) | Mean | 490.72 | 726.959 | 1553.08 | 158328 |
|  | CV % | 35 | 64 | 42 | 109 |
| CL/F (L/h) | Mean | 376.22 | 363.21 | 685.48 | 820.32 |
|  | CV % | 82 | 53 | 27 | 99 |

Summary of statistical analysis of bioavailability and dose proportionality -

| Pharmacokinetic Parameter | Summary Statistic | Simvastatin | Simvastatin Acid | Fluvastatin | Pravastatin |
| --- | --- | --- | --- | --- | --- |
| $Log_{10} AUC_{0-8}$ | Ratio of means | 1.867 | 1.481 | 2.437 | 2.174 |
|  | 90% CI | 1.582-2.203 | 1.203-1.824 | 1.671-3.553 | 1.092-4.325 |
| $Log_{10} C_{max}$ | Ratio of means | 2.087 | 1.487 | 2.21 | 2.715 |
|  | 90% CI | 1.830-2.381 | 0.976-2.268 | 1.461-3.336 | 1.051-7.011 |
| $T_{max}$ | Z | 0 | -1.84 | -0.56 | 0.00 |
|  | p value | 1.00 | 0.065 | 0.577 | 1.00 |
| $t_{1/2}$ | t | -0.93 | 1.21 | -3.01 | 0.98 |
|  | p value | 0.384 | 0.264 | 0.02 | 0.346 |

Simvastatin

Figure 1:
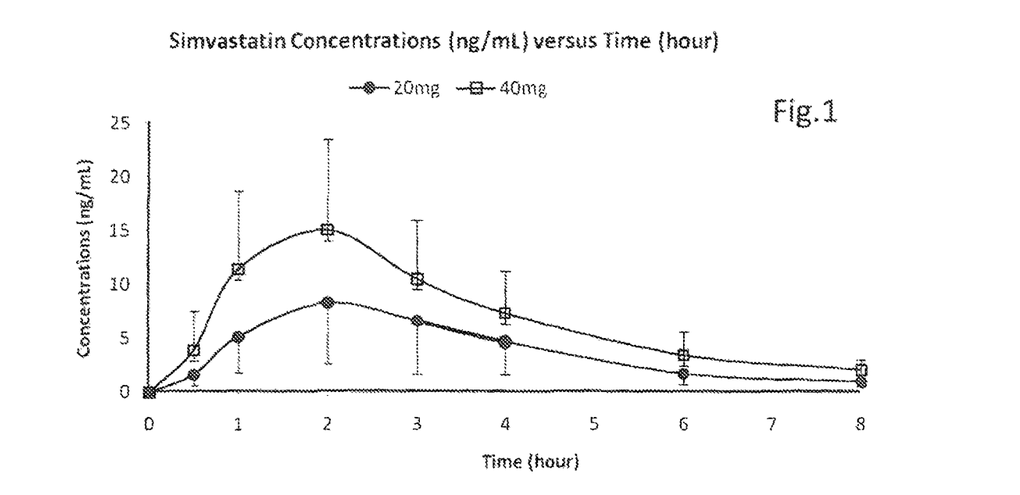
FIG. 1 shows the absorption profile after sublingual delivery of 20 mg and 40 mg of simvastatin.
Figure 2:
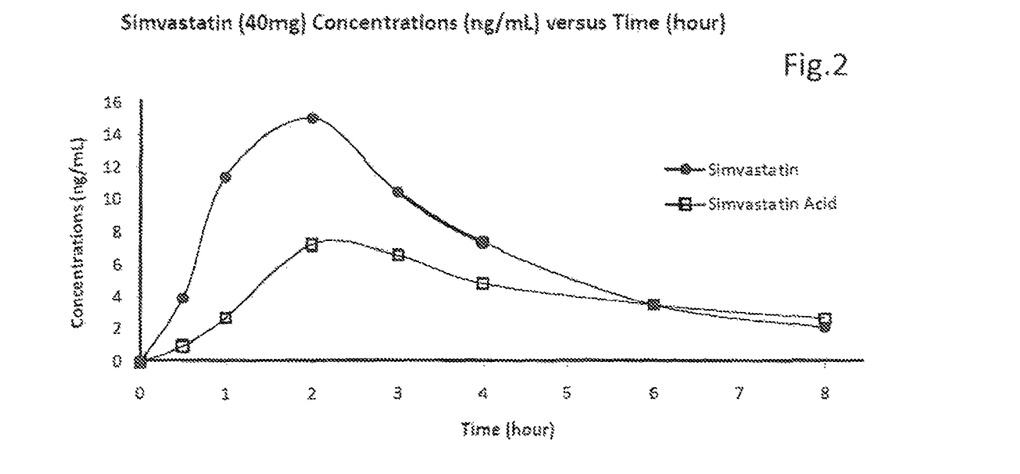
FIG. 2 shows the absorption profile after sublingual delivery of 40 mg of simvastatin and 40 mg of simvastin acid.
Figure 3:
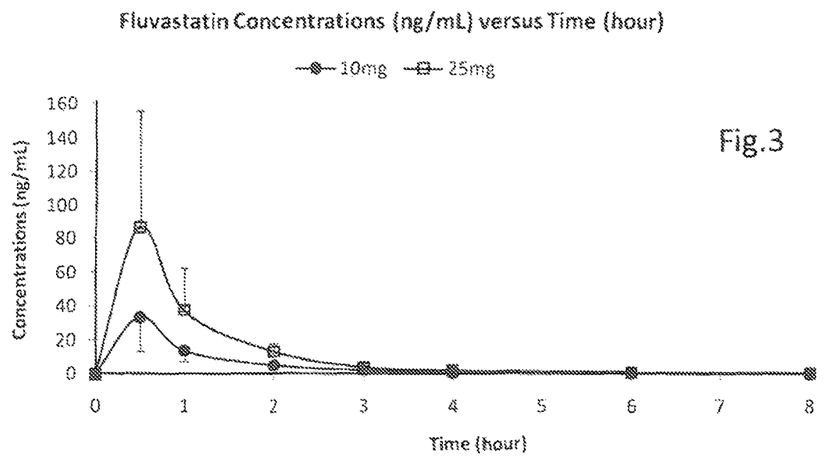
FIG. 3 shows the absorption profile after sublingual delivery of 20 mg and 40 mg of fluvastatin.
Figure 4:
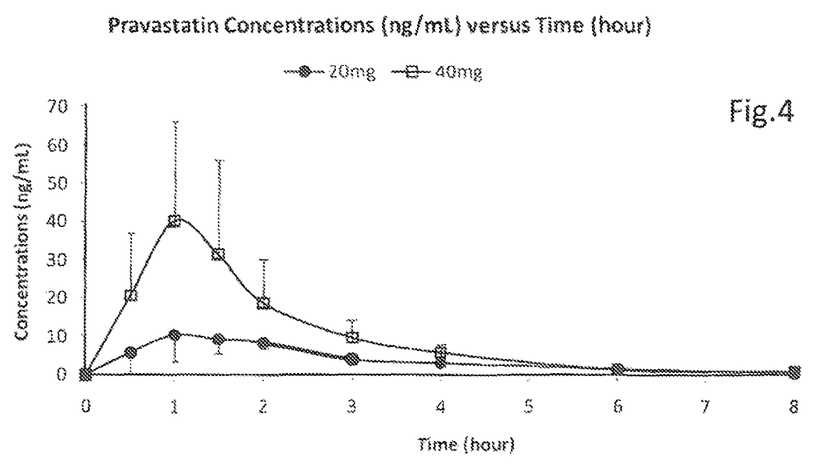
FIG. 4 shows the absorption profile after sublingual delivery of 20 mg and 40 mg of pravastatin.

Simvastatin is successfully absorbed following sublingual administration. There was no difference in the rate of absorption between the two dose levels, with the $T_{max}$ being 1.88 hours for both treatments. Likewise the reported half life $t_{1/2}$ was similar for both treatments at 1.8 and 1.9 hours for the 20 mg and 40 mg formulations respectively. The difference was not statistically significant (p=0.384). However, as this study was designed to evaluate absorption, it is apparent from the plasma concentration-time plots, that the sampling period may have been too short to have fully characterised the elimination phase. The value reported may represent in part the absorption and/or distribution phase, in which case, the $t_{1/2}$ and AUC would be biased downwards.

For the parent molecule, simvastatin, the ratio of the means (90% CI) of the log transformed $AUC_{0-8}$ for 40 mg compared to 20 mg was 1.867 (1.582-2.203), slightly outside the bioequivalence range. The ratio of the means (90% CI) for the log transformed $C_{max}$ was 2.087 (1.830-2.381), which is in the bioequivalence range. There was no difference in $T_{max}$ at 1.88 h for both treatments. The differences between the $t_{1/2}$ were also not statistically significant (p=0.384).

For simvastatin acid, the ratio of the means (90% CI) of the log transformed $AUC_{0-8}$ for 40 mg compared to 20 mg was 1.481 (1.203-1.824)). The ratio of the means (90% CI) for the log transformed $C_{max}$ was 1.487 (0.976-2.268). Neither parameter was within the bioequivalence range, indicating that they are less than dose proportional. $T_{max}$ was longer in the 40 mg group but the difference was not statistically significant. The differences between the $t_{1/2}$ were also not statistically significant (p=0.264).

For the conversion of simvastatin to simvastatin acid, the metabolite ratio of the parameter $AUC_{0-\infty}$ was 84.5% and 80% for the 20 mg and 40 mg formulations respectively. For the $C_{max}$ the respective parameters were 68% and 48%. Surprisingly, it appears that the conversion of sublingual simvastatin to the active form, simvastatin acid, is higher than the corresponding conversion rates following oral administration.

Fluvastatin

Fluvastatin sublingual spray is rapidly absorbed following administration, with the $T_{max}$ of both treatments being similar at 0.5 hours. Fluvastatin appears to be rapidly distributed. The $t_{1/2}$ was 1.18 and 1.4 hours for the 10 mg and 25 mg treatments respectively. This difference was statistically significant (p=0.02). The maximal fluvastatin plasma concentration ($C_{max}$) was 34.18 ng/mL and 88.01 ng/mL for 10 mg and 25 mg, respectively. The ratio of the means (90% CI) for the log transformed $C_{max}$ was 2.21 (1.461-3.336). The $AUC_{0-8}$ was 36.30 ng·h/mL and 89.90 ng·h/mL for the 10 mg and 25 mg treatments respectively. The ratio of the means (90% CI) of the log transformed $AUC_{0-8}$ for 25 mg compared to 10 mg was 2.437 (1.67-3.555). The confidence intervals for both parameters are too wide to conclude dose proportionality between the treatments. The infrequent sampling during the absorption phase may have underestimated the $C_{max}$ and AUC.

Pravastatin

Pravastatin sublingual spray is successfully absorbed with the $T_{max}$ of 1.3 hours for both treatments. The $t_{1/2}$ was similar for both the 20 mg and 40 mg pravastatin sublingual sprays, at 1.58 and 1.32 hours respectively. The maximal pravastatin plasma concentration ($C_{max}$) was 12.32 ng/mL and 44.51 ng/mL for 20 mg and 40 mg, respectively. The ratio of the means (90% CI) for the log transformed $C_{max}$ was 2.715 (1.051-7.012). The $AUC_{0-\infty}$ was 31.16 ng·h/mL and 80.58 ng·h/mL for the 20 mg and 40 mg treatments respectively. The ratio of the means (90% CI) of the log transformed $AUC_{0-8}$ for 40 mg compared to 20 mg was 2.174 (1.092-4.325). The confidence intervals were very wide, therefore dose proportionality could not be concluded. Two subjects were excluded from the PK analysis for the 20 mg dose and 1 subject was excluded from the 40 mg treatment due to undetectable plasma concentrations.

General

The variability in absorption between individuals appears to be reduced when using transmucosal delivery when compared to the data in the art relating to oral delivery, especially with respect to simvastatin.

Safety

Overall, both doses of simvastatin sublingual spray, fluvastatin sublingual spray, and pravastatin sublingual spray were found to be safe and well tolerated. No subject experienced local events which were related to treatment (apart from taste). There were very few treatment-emergent AEs reported generally, none for the pravastatin treatment group, only one AE after treatment with 40 mg simvastatin and with both doses of fluvastatin (5 related and 2 unrelated), all of which were of mild severity and apart from one AE which was resolved with paracetamol, all other AEs resolved spontaneously without any intervention by the end of the study. There were no clinically significant changes in vital signs, ECG parameters, physical examinations or clinical laboratory evaluations. The taste acceptance was generally good, although there were reports of very unpleasant taste. At the later time points, no taste was reported by any of the subjects. It can be concluded that both doses of simvastatin, fluvastatin, and pravastatin sublingual spray were safe and well tolerated in healthy male subjects.

The invention claimed is:

1. A method of preventing cardiovascular disease or treating hypercholesterolaemia, dyslipidaemia, or cardiovascular disease; or an effect of any of these conditions, in a human individual, comprising delivering a composition by transmucosal sublingual or transmucosal buccal administration as a spray wherein said composition comprises a statin selected from the group consisting of simvastatin, atorvastatin, lovastatin, pitavastatin, or a salt thereof, a carrier that comprises an oil that comprises a glyceride, wherein said statin is solubilised in said carrier, and from about 5% to about 35% v/v of an ethanol co-solvent.

2. The method of claim 1 wherein said oil comprises a triglyceride.

3. The method of claim 2 wherein said oil comprises a medium chain triglyceride (Ph Eur).

4. The method of claim 1 wherein said oil comprises a macrogolglyceride.

5. The method of claim 4 wherein said oil comprises caprylocaproyl macrogolglycerides (Ph Eur).

6. The method of claim 1, wherein the composition further comprises a preservative.

7. The method of claim 6 wherein said preservative is selected from the group consisting of ethanol, potassium sorbate, benzalkonium chloride, methyl, ethyl or propyl parahydroxybenzoate, a sodium salt thereof, and mixtures thereof.

8. The method of claim 1, wherein the composition further comprises an antioxidant.

9. The method of claim 1, wherein the composition further comprises a flavoring agent and/or a sweetener.

10. The method of claim 9 wherein the composition further comprises a lipophilic flavoring agent.

11. The method of claim 10 wherein said lipophilic flavoring agent comprises menthol, vanillin or an essential oil.

12. The method of claim 11 wherein said essential oil comprises orange oil, lemon oil, clove oil, peppermint oil, spearmint oil or aniseed oil.

13. The method of claim 1 wherein the individual:
a. cannot, or is unwilling to, ingest tablets, or
b. has a gastrointestinal condition or gastrointestinal obstruction, or
c. has reduced consciousness, or
d. is 10 years old or less.

14. The method of claim 1 wherein:
a. multiple administrations are given and there is a low level of variability in absorption of the composition by the individual for different administrations, or
b. a time to maximal plasma concentration (Tmax) is less than 2 hours or
c. a period of time between preparation of the composition and administration to the individual is at least 6 months or
d. the composition is administered for treatment of homozygous familial hypercholesterolaemia, or
e. the composition is administered for reduction of cardiovascular mortality and morbidity in patients with atherosclerotic cardiac disease or diabetes mellitus.

15. The method of claim 1 wherein the statin is simvastatin.

16. The method of claim 1 wherein the statin is present in the composition at a concentration of at least 5 mg/ml.

17. The method of claim 1 wherein the statin is present in the composition at a concentration of at least 25 mg/ml.

18. The method of claim 1 wherein no more than about 1000 microliters of the composition is delivered in a single dose.

19. A method of preventing cardiovascular disease or treating hypercholesterolaemia, dyslipidaemia, or cardiovascular disease; or an effect of any of these conditions, in a human individual, comprising delivering a composition by transmucosal sublingual or transmucosal buccal administration as a spray wherein the composition comprises at least about 80 mg/ml simvastatin or a salt thereof, a medium chain triglyceride (Ph Eur), and from about 5% to about 35% v/v ethanol.

20. The method of claim 1 wherein the statin is present in the composition at a concentration of at least about 80 mg/ml.

* * * * *